United States Patent
Lu et al.

(10) Patent No.: US 8,742,154 B2
(45) Date of Patent: Jun. 3, 2014

(54) BLOCK ABA SILICONE POLYALKYLENEOXICIE COPOLYMERS, METHODS OF PREPARATION, AND APPLICATIONS FOR EMPLOYING THE SAME

(75) Inventors: Ning Lu, Chappaqua, NY (US); Anne Dussaud, Tarrytown, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 231 days.

(21) Appl. No.: 13/297,931

(22) Filed: Nov. 16, 2011

(65) Prior Publication Data

US 2013/0123529 A1    May 16, 2013

(51) Int. Cl.
*C07F 7/10* (2006.01)
*C07F 7/08* (2006.01)

(52) U.S. Cl.
CPC ............... *C07F 7/0838* (2013.01); *C07F 7/10* (2013.01)
USPC ...................................................... 556/423

(58) Field of Classification Search
CPC ........................................................ C07F 7/10
USPC ...................................................... 556/423
See application file for complete search history.

(56) References Cited

U.S. PATENT DOCUMENTS

| 3,761,444 | A  | 9/1973  | Mendicino |
| 4,101,272 | A  | 7/1978  | Guise et al. |
| 5,807,956 | A  | 9/1998  | Czech |
| 5,981,681 | A  | 11/1999 | Chech |
| 6,475,568 | B1 | 11/2002 | Czech |
| 7,851,548 | B2 | 12/2010 | Anyanwu et al. |
| 8,013,097 | B2 | 9/2011  | Kennan et al. |
| 2010/0048795 | A1 | 2/2010 | Kennan et al. |
| 2012/0088843 | A1* | 4/2012 | Chang et al. ............... 514/772.3 |

FOREIGN PATENT DOCUMENTS

GB    1213779    11/1970

OTHER PUBLICATIONS

Murachashvili et al. "Carbon-functional oligoorgano-siloxanes: Structure, reaction ability and property". New perspectives in Chemistry and Biochemistry (2002), p. 81-88. Editor Zaikov, E.G.. Nova Science Publishers, Inc.: Hauppauge, N.Y. (Abstract).*
U.S. Appl. No. 13/297,926, Dussaud et al., filed Nov. 16, 2011 (claims enclosed).

* cited by examiner

*Primary Examiner* — Yong Chu
(74) *Attorney, Agent, or Firm* — Dominick G. Vicari; Joseph S. Ostroff

(57) ABSTRACT

There is provided herein a linear tri-block copolymer having the average formula (1):

ABA    (1)

wherein A is a polyalkyleneoxide unit or an aliphatic modified polyalkyleneoxide unit both of the general formula: $R^5O(C_aH_{2a}O)_dY$ and wherein B is an internal polysiloxane unit of the general formula:

$[X(C_aH_{2a}O)_bR^2[SiO(R^1)_2]_cSi(R^1)_2R^2(OC_aH_{2a})_bX]$ wherein X and Y are divalent organic groups selected from a secondary amine or a tertiary amine and a ring-opened epoxide, such that when X is a ring-opened epoxide, Y is a secondary or tertiary amine, and when Y is a ring-opened epoxide, X is a secondary or tertiary amine. In addition, there is provided herein a method of making a linear tri-block copolymer having the average formula (1) and personal care and softener compositions comprising the same, specifically a hair conditioner.

26 Claims, No Drawings

BLOCK ABA SILICONE POLYALKYLENEOXICIE COPOLYMERS, METHODS OF PREPARATION, AND APPLICATIONS FOR EMPLOYING THE SAME

This application incorporates by reference the entire contents of the application entitled ASSOCIATION PRODUCT OF AMINO FUNCTIONAL HYDROPHOBIC POLYMERS WITH HYDROPHILIC POLYMERS CONTAINING ACID GROUPS, METHODS OF PREPARATION, AND APPLICATIONS FOR EMPLOYING THE SAME, filed on Nov. 16, 2011, which has the same inventors and assignee as herein.

The present invention relates to a linear block ABA silicone polyalkyleneoxide copolymer comprising internal silicone units and further comprising polyalkyleneoxide units wherein the copolymer is capped with the polyalkyleneoxide units.

BACKGROUND OF THE INVENTION

Hair care rinse-off products are commonly used to condition hair and improve hair combability because such products are convenient to use and leave hair with a clean feel.

It is known within the industry that high molecular weight non-hydrolyzable linear random block aminosilicone-polyalkyleneoxide copolymers can improve tactile properties of treated fiber and textile substrates. However, the existing high molecular weight copolymers of this type are impractical due to their increased viscosities, which presents issues with the handling and formulation of these copolymers as textile enhancers and conditioning agents for hair care and skin care.

Therefore, it would be desirable to have a thickened aqueous system that provides conditioning, shine-enhancement and clean after-feel at the same time.

SUMMARY OF THE INVENTION

The present invention discloses in one embodiment, a linear tri-block copolymer having the average formula (1):

$$ABA \qquad (1)$$

wherein A is a polyalkyleneoxide unit or an aliphatic modified polyalkyleneoxide unit both of the general formula:

$$R^5O(C_aH_{2a}O)_dY$$

and wherein B is an internal polysiloxane unit of the general formula:

$$[X(C_aH_{2a}O)_bR^2[SiO(R^1)_2]_cSi(R^1)_2R^2(OC_aH_{2a})_bX]$$

wherein $R^1$ is an alkyl containing from 1 to about 4 carbon atoms,
$R^2$ is a divalent organic moiety containing from 1 to about 30 carbon atoms, specifically 1 to about 10 carbon atoms
each a in unit A and unit B is independently an integer of from about 2 to about 4, each b is independently 0 or an integer of from 1 to about 100, c is an integer of from 1 to about 1000,
$R^5$ is of the formula
  $(C_nH_{2n+1})$— with n=1-30, or of the formula
  $(C_nH_{2n-1})$— with n=2-30, or of the formula
  $(C_nH_{2n-3})$— with n=4-30,
d is 0 or an integer of from 1 to about 100, provided that the sum of all the b values and the d value is an integer of from 1 to about 100,
X and Y are divalent organic groups selected from a secondary amine or a tertiary amine and a ring-opened epoxide, such that when X is a ring-opened epoxide, Y is a secondary or tertiary amine, and when Y is a ring-opened epoxide, X is a secondary or tertiary amine.

There is also disclosed herein in another embodiment, a method for making a linear tri-block copolymer having the average formula (1) described above, wherein the method comprises reacting a compound of the general formula (2): $Q(C_aH_{2a}O)_bR^2[SiO(R^1)_2]_cSi(R^1)_2R^2(OC_aH_{2a})_bQ$ and a compound of the general formula (3): $R^5O(C_aH_{2a}O)_dZ$, wherein $R^1$, $R^2$, $R^5$, a, b, c and d are as defined and each Q independently and Z is either a primary or secondary amine, or an epoxy-containing group, with the proviso that if Q is a primary or secondary amine, Z is epoxy-containing group, and if Z is a primary or secondary amine, then Q is an epoxy-containing group.

In addition, there are also disclosed various personal care and softener compositions comprising the linear tri-block copolymer of the average formula (1) described above.

DETAILED DESCRIPTION OF THE INVENTION

A. Copolymer Structure

The linear triblock copolymers ABA of the present invention have polyalkyleneoxide units or aliphatic modified polyalkyleneoxide A units of the general formula: $R^5O(C_aH_{2a}O)_dY$ and polysiloxane B units of the general formula: $[X(C_aH_{2a}O)_bR^2[SiO(R^1)_2]_cSi(R^1)_2R^2(OC_aH_{2a})_bX]$ wherein the polyalkyleneoxide A units cap the linear triblock copolymer structure.

As described above, $R^1$ is an alkyl containing from 1 to about 4 carbon atoms, specifically methyl, $R^2$ is a divalent organic moiety containing from 1 to about 30 carbon atoms, specifically 1 to about 10 carbon atoms, more specifically, 2 to about 6 carbon atoms each a in unit A and unit B is independently an integer of from about 2 to about 4, specifically 2 to 3, each b is independently 0 or an integer of from 1 to about 100, specifically 1 to about 8, more specifically 1 to about 4, c is an integer of from 1 to about 1000, specifically 1 to about 500, more specifically 1 to about 100,
  $R^5$ is of the formula
  $(CnH_{2n+1})$— with n=1-30, or of the formula
  $(C_nH_{2n-1})$— with n=2-30, or of the formula
  $(C_nH_{2n-3})$— with n=4-30,
d is 0 or an integer of from 1 to about 100, provided that the sum of all the b values and the d value is an integer of from 1 to about 100, specifically about 10 to about 50

X and Y are divalent organic groups selected from a secondary amine or a tertiary amine and a ring-opened epoxide, such that when X is a ring-opened epoxide, Y is a secondary or tertiary amine, and when Y is a ring-opened epoxide, X is a secondary or tertiary amine.

The total number of ABA repeating units is limited only by the ability to handle high viscosity material, since the viscosity increases as does the number of repeating units, but in one embodiment there is only one repeat unit such that there is one B unit capped by two A unit in a linear triblock structure. In another embodiment there is at least two ABA repeat units and up to about 1000 ABA repeat units.

The ring opened epoxides, represented by either X or Y, may be aliphatic, cycloaliphatic, or aromatic. They also contain hydroxy groups and may contain an ether linkage. Preferably the ring opened epoxide is chosen from the following:

—$CH_2CH(OH)(CH_2)_xCH(OH)CH_2$—,

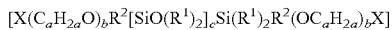—$CH[CH_2OH](CH_2)_xCH[CH_2OH]$—,

—CH$_2$CH(OH)(CH$_2$)$_v$CH[CH$_2$OH]—,

—(CH$_2$)$_v$OCH$_2$CH(OH)CH$_2$—, and

—(CH$_2$)$_v$OCH$_2$CH(CH$_2$[OH])—, wherein v is an integer of from about 2 to about 6.

Alternatively, the ring opened epoxides may be derived from the epoxycyclohexyl alkylene group containing from about 2 to about 20 carbon atoms in the alkylene moiety. In one embodiment, the epoxycyclohexyl alkylene groups is ω-(3,4-epoxycycohexyl)alkylene. In one other embodiment, the epoxycyclohexyl alkylene group is selected from the group consisting of β-(3,4-epoxycyclohexyl)ethylene, β-(3,4-epoxycyclohexyl)-β-methylethylene, and β-(3,4-epoxy-4-methylcyclohexyl)-β-methylethylene.

The amines, represented by either X or Y, are secondary or tertiary amines. More specifically, the amines may be of the general formula:

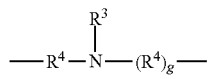

wherein R$^3$ may be H, an alkyl or alkenyl group containing from 1 to about 30 carbon atoms, specifically where R$^3$ is methyl, and R$^4$ is a divalent alkylene, divalent cycloaliphatic alkylene or a divalent aralkylene group, specifically of from 1 to about 20 carbon atoms, any of which divalent groups may include heteroatoms, and g is 0 or 1. In one specific embodiment, R$^4$ is a divalent alkylene of less than ten carbons. The moieties comprising R$^3$ specifically comprise from one to about twenty carbon atoms, e.g., methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, methoxy, ethoxy, propoxy, butoxy, phenyl, biphenyl, naphthyl, tolyl, xylyl, anthracyl, methoxyphenyl, isomers of the foregoing, and the like.

In one embodiment R$^2$ is a divalent hydrocarbon group with at least one carbon, which may have hydroxy substitutions thereon and/or include an ether linkage. R$^2$ specifically contains less than ten carbons. In one specific embodiment, within a particular ABA linear triblock copoymer each R$^1$, R$^2$, R$^3$, R$^4$ and R$^5$ may be the same or different.

In one other embodiment herein, the polyoxyalkylene blocks represented by (C$_a$H$_{2a}$O) or (OC$_a$H$_{2a}$) may be made up of ethylene oxide (a=2), propylene oxide (a=3) and butylene oxide (a=4) in a random or blocked fashion. The ratio among such oxides is not of particular importance, but may be adjusted as required for the desired solubility parameters of the resulting linear triblock copolymer ABA.

The molecular weight of the linear triblock copolymer ABA can be modified by varying the molar ratio of the epoxy component to amino component, by varying the number of oxyalkylene units and the number of siloxy groups within the polysiloxane blocks (B units). Although it is important to generate materials with high molecular weight because properties essential to the application, such as softness and durability, are dependent upon the molecular weight of the polymer, it is also essential to produce, non-crosslinked structures, i.e., only linear molecules.

Another important factor controlling the properties of the linear triblock copolymers is relative silicone content in the molecule, i.e., the values of c, and (b+d). Higher silicone content copolymers are usually more hydrophobic, therefore less water-soluble and impart better softness. A specific ratio of c to (b+d) is 10:1 to 1:10, and more specifically 2:1.

B. Method of Manufacture

Preparation of the linear triblock copolymer(s) of the present invention is by reacting a compound of the general formula (2):

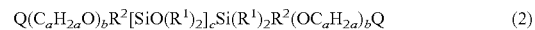  (2)

and a compound of the general formula (3):

  (3)

wherein R$^1$, R$^2$, R$^5$, a, b, c and d are as defined and each Q independently and Z is either a primary or secondary amine, or an epoxy-containing group, with the proviso that if Q is a primary or secondary amine, Z is epoxy-containing group, and if Z is a primary or secondary amine, then Q is an epoxy-containing group. These compounds may be manufactured as is known in the art or are commercially available.

In an exemplary method, α,ω-hydrogenpolysiloxanes of the general formula (4): H[SiO(R$^1$)$_2$]$_c$Si(R$^1$)$_2$H are reacted with the unsaturated epoxides with a terminal olefinic bond, such as the non-limiting example of allyl glycidyl ether, in the presence of a hydrosilation catalyst, such as for example hexachloroplatinic acid, at elevated temperature, to produce epoxy endblocked polysiloxanes. Such procedures are known in the art as indicated in U.S. Pat. No. 3,761,444 or British Patent No. 1,213,779, the contents of which are incorporated by reference herein.

Examples of suitable epoxides with terminal olefinic groups are given below:

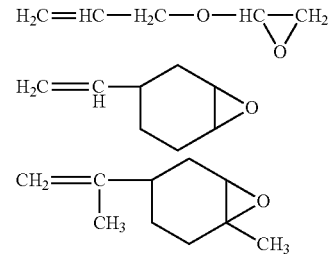

In the second step, the epoxy endblocked polysiloxanes (such as those of the general formula (2)) are reacted with polyalkyleneoxides terminated with primary or secondary amino groups, such as compounds of the general formula (3) described above. Some such aminopolyalkyleneoxides are selected from the group consisting of Jeffamine® M-600, Jeffamine® M-1000, Jeffamine® M-2005 and Jeffamine® XTJ-682 and may be of the formula:

wherein R is R$^5$ and a and b are as defined.

The reaction of the second step can be carried out in a suitable solvent, such as alcohol or mixture of alcohol and water at reflux. Typically, epoxy endblocked polysiloxanes are added to the solution of the amine in the reaction solvent. Other methods of manufacturing the present structures will be clear to one of skill in the art.

For practical purposes, the reaction is carried out with a 1 to 20%, preferably 1 to 10%, excess of the amine containing species. Despite the fact that the excess of the amine is used during the preparation of the copolymers, it is possible that the epoxy end group on the polysiloxane can undergo side reactions with the solvent, water or alcohol to form the corresponding diol or ether alcohol.

After the second reaction, the solution of the linear triblock copolymer can be neutralized by a direct addition of a Bronstedt acid such as acetic acid, citric acid or tartaric acid and/or undergo solvent exchange with a non-flammable solvent such as water, propylene glycol, dipropylene glycol and dipropylene glycol methyl ether. In one embodiment, the linear triblock copolymer can be isolated by distilling off the solvent at atmospheric or reduced pressure; depending on the molecular weight and ethylene oxide content of the copolymer it may be a viscous oil or a wax.

C. Copolymer Uses

The linear triblock copolymers described herein are primarily intended as softeners for substrates, especially hair, fibers, and textiles. While these copolymers can be used neat, for ease of application, they are usually applied to the substrates dissolved, dispersed, or emulsified in a suitable liquid medium. Specifically, they are applied to the substrate from an aqueous solution, emulsion, or suspension. They may also be applied as a solution in a non-aqueous solvent, such as isopropanol, or in a liquid in which the copolymer is miscible. More preferably, the linear triblock copolymer is applied to the substrate as an aqueous dispersion.

Aqueous emulsions of the linear triblock copolymers can be prepared by combining the copolymer with one or more emulsifiers, such as nonionic surfactants, and diluted with water to a desired concentration. Nonionic surfactants commonly employed in such emulsions can include, for example, TERGITOL surfactants, available from Union Carbide Chemicals and Plastics Co., Inc.

Stable aqueous dispersions of the linear triblock copolymers can, for example, be prepared by directly blending or mixing a solution of the linear triblock copolymer in a water miscible solvent, such as isopropanol, propylene glycol, dipropylene glycol, or dipropylene glycol methyl ether, with water to obtain the desired copolymer level.

Once prepared, the dispersions, emulsions, or solutions can be applied to a substrate by any conventional means, such as by spraying, dipping, kiss roll application, or other application method typically employed in fiber, hair, or textile treatment. The substrates that can be treated with the linear triblock copolymers herein are exemplified by natural fibers, such as hair, cotton, silk, flax, cellulose, paper (including tissue paper), and wool; synthetic fibers, such as polyester, polyamide, polyacrylonitrile, polyethylene, polypropylene, and polyurethane; and inorganic fibers, such as glass or carbon fibers. Fabric substrates that can be treated with the linear triblock copolymers described herein are exemplified by fabrics produced from the above-mentioned fibrous materials or blends thereof.

In general, the dispersions, emulsions, or solutions are applied to hair, fiber, or textile substrates such that up to 5 percent, specifically 0.25 to 2.5 percent of the linear triblock copolymer by weight of the dry substrate remains on the substrate. Optionally, other additives commonly used to treat hair or textile substrates can be employed along with the linear triblock copolymers described herein, including but not limited to, additional surfactants, deposition polymers, quaternary conditioning agents, curing resins, preservatives, dyes, colorants, formularies, and the like.

Moreover, compositions comprising the copolymers of the present invention can be used in a personal care formulation, including a cleanser, a body wash, a soap, a lotion, a cream, shaving cream, hair spray, a conditioner, a shampoo, a deodorant, a moisturizer, sunblock, and the like.

The copolymers of the present invention can be formulated into these products together with one or more anionic surfactants, one or more amphoteric surfactants, one or more nonionic surfactants, and/or one or more deposition polymers or thickeners.

A typical shampoo formulation comprises from about 3 to about 30 weight percent of an anionic and/or amphoteric surfactant component, from about 0.1 to about 10 weight percent of a nonionic surfactant component, together with from about 0.1 to about 20 weight percent of one or more copolymers of the present invention, and water. The formulation also preferably comprises an effective amount, on the order of from about 0.1 to about 5 weight percent, of a thickener. Examples of suitable thickeners include, for example, sodium alginate, gum arabic, polyoxyethylene, guar gum, hydroxypropyl guar gum, cellulosics, such as methyl cellulose, methylhydroxypropyl cellulose, and hydroxypropylcellulose, starch derivatives, such as hydroxyethylamylose, locust bean gum, polysaccharides, and the like.

In one embodiment herein there is also provided a silicone composition, specifically a silicone network composition comprising the linear triblock copolymer described herein.

In one specific embodiment herein there is provided a hair conditioner comprising the linear triblock copolymer described herein.

The advantages and the important features of the present invention will be more apparent from the following examples.

EXAMPLES

The linear triblock copolymers described herein have been successfully applied as a conditioning agent for hair products and surprisingly show better conditioning effect than regular and random block amino-polysiloxane-polyalkyleneoxide copolymers as well as conventional amino silicones.

Preparation of the Linear Triblock Copolymers:
Examples 1-7 were prepared as follows:

First, an epoxy-endblocked polysiloxane was prepared as follows: in a 2-liter four-neck flask equipped with stirrer, additional funnel and reflux condenser, α,ω-hydrogensiloxane of the general formula $H[SiO(R^1)_2]_c Si(R^1)_2 H$ was heated to 80° C. (Structures and charges are provided in Table-1). A slow addition of allyl glycidyl ether (charges are provided in Table-1) was started at 80° C. after chloroplatinic acid (5-10 ppm as Pt) was added to the pot. The temperature was maintained at 80° C. to 90° C. until no Si—H could be detected by the Fermentation tube test. The excess allyl glycidyl ether was removed by vacuum stripping at 130° C. and 20 mmHg. The resulting epoxy fluid was mixed with 0.5 wt % of Celite and then filtered through a pressure filter. The product was characterized by its epoxy content.

TABLE 1

Charges for the Preparation of the Epoxy-endblocked Polysiloxanes

| Value of c | SiH charge (g) | Allyl glycidyl ether charge (g) | Desination of the epoxy fluid | Epoxy content (meq/g) | Name of epoxy siloxane |
|---|---|---|---|---|---|
| 50 | 1000 | 69.29 | D50 | 0.51 | I |
| 100 | 1000 | 34.94 | D100 | 0.29 | II |
| 380 | 1000 | 9.48 | D380 | 0.07 | III |

Second, the amino-functionalized polymer with a formula of $R(OCH_2)_a[OCH(CH_3)]_b NH_2$ (specific structures shown in Table 2 and amounts shown in Table 3) and a sufficient amount of isopropanol to make a 50% of solution of the final copolymer were charged in a four-neck flask equipped with a stirrer, addition funnel, reflux condenser and thermocouple. The temperature of the reaction mixture was adjusted to 80° C. and an epoxy-terminated polysiloxane (Charges are provided in Table 3) was added from an addition funnel. The reaction was completed when the epoxy functionality, determined by titration, was consumed.

TABLE 2

Structure of the amino modified polymer with a formula of $R(OCH_2CH_2)_a[OCH(CH_3)CH_2]_bNH_2$

| Name | a | b | R |
|---|---|---|---|
| Jeffamine M-2070 | 31 | 10 | —$CH_3$ |
| Jeffamine M-1000 | 19 | 3 | —$CH_3$ |
| Jeffamine M-600 | 1 | 9 | —$CH_3$ |
| Jeffamine M-2005 | 6 | 29 | —$CH_3$ |
| Jeffamine XTJ-682 | 0 | 3 | —$C_{12}H_{25}$ |
| Oleylamine | 0 | 0 | —$C_{18}H_{35}$ |

TABLE 3

Charges for the Preparation of the ABA copolymers

| ABA copolymer | Name of epoxy siloxane | Charge of epoxy polysiloxane (g) | Amino modified polymer | Charge of amino modified polymer (g) | Designation of the ABA copolymer |
|---|---|---|---|---|---|
| D100 | II | 84.48 | Jeffamine M-2070 | 50.00 | Example 1 |
| D100 | II | 61.45 | Jeffamine M-1000 | 18.00 | Example 2 |
| D50 | I | 62.47 | Jeffamine M-600 | 18.00 | Example 3 |
| D380 | III | 274.29 | Jeffamine M-2005 | 40.00 | Example 4 |
| D100 | II | 110.34 | Jeffamine XTJ-682 | 40.00 | Example 5 |
| D380 | III | 137.14 | Jeffamine XTJ-682 | 12.00 | Example 6 |
| D380 | III | 102.86 | Oleylamine | 2.00 | Example 7 |

Hair conditioning properties of the various linear triblock copolymers (examples 1-7) and those of the comparative examples were tested in a side-by-side comparison. Human hair was treated with Silsoft® A-843 (Comparative Example 1), Silsof® A-553 (Comparative Example 2), an amino-end-blocked polysiloaxane (Comparative Example 3) and linear triblock copolymer Examples 1-7 of the present disclosure. All of the polymer samples were diluted in isopropanol to make the hair conditioning solutions. Each conditioning solution contained 0.035 wt % of polymer. Combing force measurements were carried out to evaluate the performance of the hair after treatment with conditioning solutions. This combing force test protocol measures the percent (%) reduction of the plateau load. The plateau load is the initial force required to comb through the hair tress with a fine teeth comb.

Hair Tress Preparation:

9 single bleached hair tresses 4 g tresses, (5" long) were purchased from Hair International Inc. Prior to washing, each tress was dipped in 0.5% aqueous sodium hydroxide solution for one minute and subsequently rinsed with running tap water. Each tress was then washed with 1 ml of 10% SLES (Sodium lauryl ether sulfate) solution and rinsed using standard washing protocol. After washing, the wet tresses were dried in an hair helmet for a few hours, combed with a fine teeth comb, and kept overnight in an environmental chamber at 50% relative humidity before combing force measurement. These clean tresses were used to measure the baseline combing force, according to the combing force protocol described below. After the baseline measurement, each of the tresses were separately treated with one of the conditioning solutions, (examples 1-7 and comparative examples 1 and 2). The condition solution was distributed evenly with a pipet on both sides of each hair tress, with a polymer loading of 250 ppm on each tress. Each tress was treated with the conditioning solution with half on each side and a polymer loading in the tress of 250 ppm. The treated hair tresses were dried in an oven at 50° C. overnight and then kept overnight in an environmental chamber at 50% relative humidity before the combing force measurement.

Dry Combing Force Measurement:

The combing force measurements were performed on a Diastron combing force apparatus, which was enclosed in a controlled humidity chamber, equilibrated at 50% relative humidity. The automatic comb speed was set to 500 mm/min. Measurements were repeated 6 times on each tress, with the first run result discarded. The results are summarized in Table 4.

TABLE 4

Combing Force Data obtained on Damaged Hair

| | Untreated | | Treated | | |
|---|---|---|---|---|---|
| Treatment Synthesis Examples | Average Plateau Load (g) | Std Dev. | Average Plateau Load (g) | Std Dev. | % Reduction |
| Example 1 | 54.3 | 5.2 | 20.1 | 6.3 | 63.8 |
| Example 2 | 118.1 | 12.0 | 62.4 | 18.1 | 47.2 |
| Example 3 | 59.6 | 10.6 | 23.2 | 7.6 | 61.0 |
| Example 4 | 113.8 | 12.6 | 43.4 | 11.6 | 61.9 |
| Example 5 | 110.6 | 11.1 | 64.2 | 17.0 | 42.0 |
| Example 6 | 104.1 | 9.7 | 44.8 | 13.7 | 57.0 |
| Example 7 | 42.9 | 7.8 | 19.7 | 7.7 | 54.0 |
| Comparative Example 1 | 51.9 | 26.6 | 34.2 | 2.9 | 34.0 |
| Comparative Example 2 | 117.0 | 27.1 | 77.5 | 12.5 | 33.8 |
| Comparative Example 3 | 194.3 | 19.0 | 119.0 | 26.3 | 38.8 |

Hair treated with the conditioning solution containing the linear triblock copolymers described herein (examples 1-7) showed significant improvement in combability as observed through the marked reduction in plateau load compared with conventional terminal amino silicone (Comparative example 3), random block $(AB)_n$ amino-polysiloxane-polyalkyleneoxide copolymer Silsoft A553 (Comparative Example 2) and regular block $(AB)_n$ amino-polysiloxane-polyalkyleneoxide copolymer Silsoft A843 (Comparative Example 3).

While the invention has been described with reference to a specific embodiment, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

The invention claimed is:

1. A linear tri-block copolymer represented by the average formula (1):

ABA  (1)

wherein A is a polyalkyleneoxide unit or an aliphatic modified polyalkyleneoxide unit both of the general formula:

$R^5(C_aH_{2a}O)_dY$ and wherein B is an internal polysiloxane unit of the general formula:

$[X(C_aH_{2a}O)_bR^2[SiO(R^1)_2]_cSi(R^1)_2R^2(OC_aH_{2a})_bX]$ wherein
$R^1$ is an alkyl containing from 1 to 4 carbon atoms,
$R^2$ is a divalent organic moiety containing from 1 to 30 carbon atoms,
each a in unit A and unit B is independently an integer of from 2 to 4,
each b is independently 0 or an integer of from 1 to 100,
c is an integer of from 1 to 1000,
$R^5$ is of the formula $(C_nH_{2n+1})$— with n=1-30, or of the formula $(C_nH_{2n-1})$— with n=2-30, or of the formula $(C_nH_{2n+3})$— with n=4-30,
d is an integer of from 1 to 100,
provided that the sum of all the b values and the d value is an integer of from 1 to 100,
X and Y are divalent organic groups selected from a secondary amine, a tertiary amine and a ring-opened epoxide, such that when X is a ring-opened epoxide, Y is a secondary or tertiary amine, and when Y is a ring-opened epoxide, X is a secondary or tertiary amine.

2. The copolymer of claim 1 wherein the ring-opened epoxide which is represented by either X or Y is aliphatic, cycloaliphatic or aromatic.

3. The copolymer of claim 1 wherein the ring-opened epoxide which is represented by either X or Y contains at least one of a hydroxyl group and an ether linkage.

4. The copolymer of claim 1 wherein the ring-opened epoxide is selected from the the group consisting of:

—$CH_2CH(OH)(CH_2)_vCH(OH)CH_2$—,

—$CH[CH_2OH](CH_2)_vCH[CH_2OH]$—,

—$CH_2CH(OH)(CH_2)_vCH[CH_2OH]$—,

—$(CH_2)_vOCH_2CH(OH)CH_2$—, and

—$(CH_2)_vOCH_2CH(CH_2[OH])$—, wherein v is an integer of from 2 to 6.

5. The copolymer of claim 1 wherein the ring opened epoxide is derived an epoxycyclohexyl alkylene group containing from 2 to 20 carbon atoms in the alkylene moiety.

6. The copolymer of claim 5 wherein the epoxycyclohexyl alkylene group is ω-(3,4-epoxycyohexyl)alkylene.

7. The copolymer of claim 5 wherein the epoxycyclohexyl alkylene group is selected from the group consisting of β-(3,4-epoxycyclohexyl)ethylene, β-(3,4-epoxycyclohexyl)-β-methylethylene, and β-(3,4-epoxy-4-methylcyclohexyl)-β-methylethylene.

8. The copolymer of claim 1 wherein the secondary or tertiary amine represented by either X or Y are of the general formula:

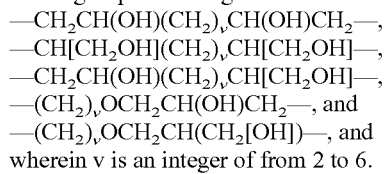

wherein $R^3$ may be H, an alkyl or alkenyl group with containing from 1 to 30 carbons, and $R^4$ is a divalent alkylene, divalent cycloaliphatic alkylene or a divalent aralkylene group, any of which divalent groups may include heteroatoms, and g is 0 or 1.

9. The copolymer of claim 8 wherein $R^3$ is methyl.

10. The copolymer of claim 8 wherein $R^4$ is a divalent alkylene group of less than 10 carbon atoms.

11. The copolymer of claim 1 wherein $R^1$ is methyl, a is 2 or 3, the sum of all the b values and the d value is from 10 to 50, c is from 10 to 100 and the ring-opened epoxide is selected from the group consisting of
—$CH_2CH(OH)(CH_2)_vCH(OH)CH_2$—,
—$CH[CH_2OH](CH_2)_vCH[CH_2OH]$—,
—$CH_2CH(OH)(CH_2)_vCH[CH_2OH]$—,
—$(CH_2)_vOCH_2CH(OH)CH_2$—, and
—$(CH_2)_vOCH_2CH(CH_2[OH])$—, and
wherein v is an integer of from 2 to 6.

12. A method for making a linear tri-block copolymer represented by the formula (1) ABA, wherein A is a polyalkyleneoxide unit or an aliphatic modified polyalkyleneoxide unit both of the general formula $R^5(C_aH_{2a}O)_dY$, and wherein B is an internal polysiloxane unit of the general formula:

$[X(C_aH_{2a}O)_bR^2[SiO(R^1)_2]_cSi(R^1)_2R^2(OC_aH_{2a})_bX]$, wherein $R^1$ is an alkyl containing from 1 to 4 carbon atoms,
$R^2$ is a divalent organic moiety containing from 1 to 30 carbon atoms,
each a in unit A and unit B is independently an integer of from 2 to 4,
each b is independently 0 or an integer of from 1 to 100,
c is an integer of from 1 to 1000,
$R^5$ is of the formula $(C_nH_{2n-1})$— with n=1-30, or of the formula $(C_nH_{2n-1})$— with N=2-30, or of the formula $(C_nH_{2n-3})$— with n=4-30,
d is an integer of from 1 to 100,
provided that the sum of all the b values and the d value is an integer of from 1 to 100,
X and Y are divalent organic groups selected from a secondary amine, a tertiary amine and a ring-opened epoxide, such that when X is a ring-opened epoxide, Y is a secondary or tertiary amine, and when Y is a ring-opened epoxide, X is a secondary or tertiary amine, wherein the method comprises:
reacting a compound of the formula (2):
$Q(C_aH_{2a}O)_bR^2[SiO(R^1)_2]_cSi(R^1)_2R^2(OC_aH_{2a})_bQ$ (2), and a compound of the general formula (3): $R^5(C_aH_{2a}O)_dZ$ (3), wherein $R^1$, $R^2$, $R^5$, a, b, c and d are as defined and each Q independently and Z is either a primary or secondary amine, or an epoxy-containing group, with the proviso that if Q is a primary or secondary amine, Z is epoxy-containing group, and if Z is a primary or secondary amine, then Q is an epoxy-containing group.

13. The method of claim 12 wherein the compound of the general formula (2) is made by reacting α,ω-hydrogenpolysiloxane of the general formula (4):

with an unsaturated epoxide containing a terminal olefinic bond, in the presence of a hydrosilylation catalyst.

14. The method of claim 12 wherein the compound of the general formula (3) is $R(OCH_2CH_2)_a[OCH(CH_3)CH_2]_bNH_2$ wherein R is $R^5$ and a and b are as defined.

15. The method of claim 12 wherein the compound of the general formula (3) is selected from the group consisting of Jeffamine® M-600, Jeffamine® M-1000, Jeffamine® M-2005 and Jeffamine® XTJ-682.

16. The method of claim 12 wherein the reaction of compounds of the formulae (2) and (3) is conducted in a 1 to about 20% excess of compound of the formula (3).

17. The method of claim 12 wherein following the reaction of compounds of formula (2) and (3) the reaction product can be neutralized by a direct addition of a Bronstedt acid and/or undergo solvent exchange with a non-flammable solvent.

18. A silicone composition comprising the copolymer of claim 1.

19. A silicone network composition comprising the copolymer of claim 1.

20. A personal care composition comprising the copolymer of claim 1.

21. A personal care composition comprising the copolymer of claim 1 wherein the personal care composition is one of a cleanser, a body wash, a soap, a lotion, a cream, shaving cream, hair spray, a conditioner, a shampoo, a deodorant, a moisturizer, and sunblock.

22. A softener composition for a substrate comprising the copolymer of claim 1 wherein the substrate is selected from the group consisting of a hair, a fiber and a textile.

23. The softener composition of claim 22 wherein the fiber is a natural fiber selected from the group consisting of cotton, silk, flax, cellulose, paper and wool.

24. The softener composition of claim 22 wherein the fiber is a synthetic fiber selected from the group consisting of polyester, polyamide, polyacrylonitrile, polyethylene, polypropylene and polyurethane.

25. The softener composition of claim 22 wherein the fiber is an inorganic fiber selected from the group consisting of glass and carbon fibers.

26. A hair conditioner comprising the copolymer of claim 1.

* * * * *